United States Patent [19]

Kojima et al.

[11] Patent Number: 5,192,647
[45] Date of Patent: Mar. 9, 1993

[54] METHOD FOR DEVELOPMENT PROCESSING OF SILVER HALIDE PHOTOGRAPHIC MATERIAL

[75] Inventors: Tetsuro Kojima; Shoji Ishiguro; Hisashi Okada; Morio Yagihara, all of Kanagawa, Japan

[73] Assignee: Fuji Photo Film Co., Ltd., Kanagawa, Japan

[21] Appl. No.: 668,688

[22] Filed: Mar. 7, 1991

Related U.S. Application Data

[63] Continuation of Ser. No. 339,443, Apr. 17, 1989, abandoned, which is a continuation of Ser. No. 112,183, Oct. 26, 1987, abandoned.

[30] Foreign Application Priority Data

Oct. 24, 1986 [JP] Japan ................. 61-252846

[51] Int. Cl.$^5$ ............................. G03C 5/26
[52] U.S. Cl. ............................. 430/448; 430/489; 430/603; 430/607; 430/613
[58] Field of Search ............. 430/440, 445, 446, 448, 430/449, 490, 611, 613, 949, 489, 603, 607

[56] References Cited

U.S. PATENT DOCUMENTS

| | | | |
|---|---|---|---|
| 3,082,088 | 3/1963 | Hellmann | 430/614 |
| 4,131,467 | 12/1978 | Bigelow | 430/614 |
| 4,311,781 | 1/1982 | Mifune et al. | 430/446 |
| 4,391,900 | 7/1983 | Toyoda et al. | 430/446 |
| 4,414,305 | 11/1983 | Nakamura et al. | 430/489 |
| 4,416,977 | 11/1983 | Ohashi et al. | 430/446 |
| 4,420,554 | 12/1983 | Ohashi et al. | 430/446 |
| 4,435,500 | 3/1984 | Okutsu et al. | 430/489 |
| 4,845,020 | 7/1989 | Itoh et al. | 430/489 |
| 4,863,830 | 9/1989 | Okutsu et al. | 430/446 |

FOREIGN PATENT DOCUMENTS

| | | |
|---|---|---|
| 645979 | 11/1950 | United Kingdom . |
| 1097548 | 1/1968 | United Kingdom . |
| 1242111 | 8/1971 | United Kingdom . |
| 1352274 | 5/1974 | United Kingdom . |
| 2106660 | 4/1983 | United Kingdom . |

OTHER PUBLICATIONS

Amines and Amino, Hackh's Chemical Dictionary, Fourth Edition, 1969, pp. 35-36.
Synthetic Organic Chemistry, Romeo B. Wagner, pp. vii, 565, 566, 568, 569, 653, 654, 733 and 821-823, 1953, John Wiley & Son, Inc.
U.S. Appln. Ser. No. 07/060,790, filed Jun. 12, 1987.
U.S. Appln. Ser. No. 07/091,928, filed Sep. 1, 1987.

Primary Examiner—Hoa V. Le
Attorney, Agent, or Firm—Sughrue, Mion, Zinn, Macpeak & Seas

[57] ABSTRACT

A method for development processing of a light-sensitive silver halide photographic material comprising a support having provided thereon at least one surface latent image type silver halide emusion layer, in the presence of a compound represented by formula (I)

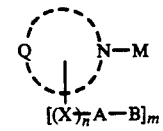

wherein Q, X, A, B, M, m and n are as defined above. The method prevents generation of developer fog without reducing sensitivity.

13 Claims, No Drawings

METHOD FOR DEVELOPMENT PROCESSING OF SILVER HALIDE PHOTOGRAPHIC MATERIAL

This is a continuation of application Ser. No. 07/339,443 filed Apr. 17, 1989, now abandoned, which is a continuation of application Ser. No. 07/112,183 filed Oct. 26, 1987, now abandoned.

FIELD OF THE INVENTION

This invention relates to a method for developing a silver halide photographic material, and more particularly to a method for development processing of a photographic material containing a surface latent image type silver halide by which developer fog can be inhibited.

BACKGROUND OF THE INVENTION

A density increase in unexposed areas of a silver halide photographic material (hereinafter referred to as a "light-sensitive material") due to development processing is called "developer fog". This phenomenon is more likely to occur when the light-sensitive material has higher sensitivity, is preserved for a longer period of time, or under severer conditions, i.e., higher temperature and higher humidity.

Further, fog is extremely apt to occur in high-temperature rapid processing or high-activity rapid processing, which is often adopted for reduction of processing time. Generation of developer fog should be minimized as it brings about deterioration of photographic properties, such as reduction in image contrast.

Conventional techniques for the inhibition of developer fog include addition of antifoggants to light-sensitive materials or a developer. A number of compounds have been proposed as antifoggants as disclosed, e.g., in Birr, *Stabilization of Photographic Silver Halide Emulsions* (Focal Press, 1974). However, these conventional antifoggants are disadvantageous in that they decrease sensitivity or gradation of the light-sensitive materials, or tend to interfere with the adsorption of a sensitizing dye onto silver halide grains, thus hindering color sensitization. Also, these disadvantages become more conspicuous as the activity of the antifoggants becomes higher. A compound is eagerly sought which can inhibit fog generation without impairing sensitivity and gradation or adversely affecting color sensitization.

SUMMARY OF THE INVENTION

One object of this invention is to provide a method for development processing by which developer fog can be inhibited effectively without reduction of sensitivity.

Another object of the invention is to provide a method for development processing by which developer fog can be inhibited without decreasing gradation of the light-sensitive material.

Yet another object of the invention is to provide a method for development processing by which developer fog can be inhibited without adversely affecting color sensitization.

It has now been found that this and other objects of the invention can be accomplished by developing a light-sensitive silver halide photographic material including a support having thereon at least one surface latent image type silver halide emulsion layer in the presence of a compound represented by formula (I):

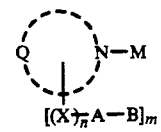

wherein Q represents an atomic group necessary for forming a 5- or 6-membered heterocyclic ring which may be fused with an aromatic carbocyclic ring or an aromatic heterocyclic ring; X represents a divalent linking group containing at least one atom selected from a carbon atom, a nitrogen atom, an oxygen atom, and a sulfur atom; A represents a linking group containing at least one group selected from a straight or branched chain alkylene group, a straight or branched chain alkenylene group, a straight or branched chain aralkylene group and an arylene group; B represents a substituted or unsubstituted amino group or a nitrogen-containing heterocyclic ring; M represents a hydrogen atom, an alkali metal atom or an ammonium group; m is 1 or 2; and n is 0 or 1.

DETAILED DESCRIPTION OF THE INVENTION

In formula (I), Q preferably represents an atomic group necessary for forming a 5- or 6-membered heterocyclic ring composed of at least one of a carbon atom, a nitrogen atom, an oxygen atom, and a sulfur atom. The heterocyclic ring may be fused to an aromatic carbocylic ring or an aromatic heterocyclic ring. Examples of the heterocyclic ring formed by Q include an indazole ring, a benzimidazole ring, a benzotriazole ring, an imidazole ring, a triazole ring, a tetrazole ring, a tetraazaindene ring, a triazaindene ring, a pentaazaindene ring, a diazaindene ring, a pyrazole ring, and an indole ring.

These heterocyclic rings may be substituted with a nitro group, a halogen atom (e.g., a chlorine atom, a bromine atom, etc.), a mercapto group, a cyano group, a substituted or unsubstituted alkyl group (e.g., a methyl group, an ethyl group, a propyl group, a t-butyl group, a methoxyethyl group, a methylthioethyl group, a methylthiomethyl group, a methoxyethoxyethoxyethyl group, a trimethylammonioethyl group, a cyanoethyl group, etc.), a substituted or unsubstituted aryl group (e.g., a phenyl group, a 4-methanesulfonamidophenyl group, a 4-methylphenyl group, a 3-methoxyphenyl group, a 3,4-dichlorophenyl group, a naphthyl group, etc), a substituted or unsubstituted alkenyl group (e.g., an allyl group, etc.), a substituted or unsubstituted aralkyl group (e.g., a benzyl group, a 4-methylbenzyl group, a phenethyl group, a 4-methoxybenzyl group, etc.), a substituted or unsubstituted alkoxy group (e.g., a methoxy group, an ethoxy group, a methoxyethoxy group, a methylthioethoxy group, etc.), a substituted or unsubstituted aryloxy group (e.g., a phenoxy group, a 4-methoxyphenoxy group, etc.), a substituted or unsubstituted alkylthio group (e.g., a methylthio group, an ethylthio group, a propylthio group, a methylthioethyl group, a methoxyethylthio group, etc.), a substituted or unsubstituted arylthio group (e.g., a phenylthio group, etc.), a substituted or unsubstituted sulfonyl group (e.g., a methanesulfonyl group, an ethanesulfonyl group, a p-toluenesulfonyl group, a methoxyethylsulfonyl group, etc.), a substituted or unsubstituted carbamoyl group (e.g., a carbamoyl group, a methylcarbamoyl group, a methoxyethylcarbamoyl group, a methylthioethylcarbamoyl group, a phenylcarbamoyl group, etc.), a substituted or unsubstituted sulfamoyl group (e.g., a sulfamoyl group, a methylsulfamoyl group, a phenylsulfamoyl group, etc.), a substituted or unsubstituted carbonamido group (e.g., an acetamido group, a benzamido group, a methoxypropionamido group, etc.), a substituted or unsubstituted sulfonamido group (e.g., a methanesulfonamido group, a benzenesulfonamido group, a p-toluenesulfonamido group, etc.), a substituted or unsubstituted acyloxy group (e.g., an acetyloxy group, a benzoyloxy group, etc.), a substituted or unsubstituted sulfonyloxy group (e.g., a methanesulfonyloxy group, etc.), a substituted or unsubstituted ureido group (e.g., a ureido group, a methylureido group, an ethylureido group, a methoxyethylureido group, a methylthioethylureido group, a phenylureido group, etc.), a substituted or unsubstituted thioureido group (e.g., a thioureido group, a methylthioureido group, a methoxyethylthioureido group, etc.), a substituted or unsubstituted acyl group (e.g., an acetyl group, a benzoyl group, a 4-methoxybenzoyl group, etc.), a substituted or unsubstituted heterocyclic group (e.g., a 1-morpholino group, a 1-piperidino group, a 2-pyridyl group, a 4-pyridyl group, a 2-thienyl group, a 1-pyrazolyl group, a 1-imidazolyl group, a 2-tetrahydrofuryl group, a tetrahydrothienyl group, etc.), a substituted or unsubstituted hydroxycarbonyl group (e.g., a methoxycarbonyl group, a phenoxycarbonyl group, a methoxyethoxycarbonyl group, a methylthioethoxycarbonyl group, a methoxyethoxyethoxyethoxycarbonyl group, etc.), a substituted or unsubstituted hydroxycarbonylamino group (e.g., a methoxycarbonylamino group, a phenoxycarbonylamino group, a 2-ethylhexyloxycarbonylamino group, etc.), a substituted or unsubstituted amino group (e.g., an amino group, a dimethylamino group, a methoxyethylamino group, an anilino group, etc.), a carboxyl group inclusive of its salt, a sulfo group inclusive of its salt, a hydroxyl group, etc., preferably each having up to 12 carbon atoms.

Preferred examples of substituents on the heterocyclic group include a halogen atom, an alkyl group, an alkoxy group, an alkylthio group, a sulfonyl group, a carbamoyl group, a sulfamoyl group, a sulfonamido group, and a ureido group, and the most preferred groups include a halogen atom, an alkyl group, and an alkoxy group.

The divalent linking group represented by X includes

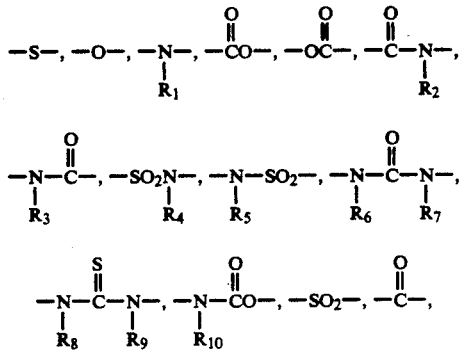

wherein $R_1$, $R_2$, $R_3$, $R_4$, $R_5$, $R_6$, $R_7$, $R_8$, $R_9$, and $R_{10}$, which may be the same or different, each represents a hydrogen atom, a substituted or unsubstituted alkyl group (e.g., a methyl group, an ethyl group, a propyl group, an n-butyl group, etc.), a substituted or unsubstituted aryl group (e.g., a phenyl group, a 2-methylphenyl group, etc.), a substituted or unsubstituted alkenyl group (e.g., a propenyl group, a 1-methylvinyl group, etc.) or a substituted or unsubstituted aralkyl group (e.g., a benzyl group, a phenethyl group, etc.). The alkyl, aryl, alkenyl and aralkyl groups represented by $R_1$ to $R_{10}$ preferably have up to 12 carbon atoms and more preferably up to 7 carbon atoms. The most preferred carbon atom range for the alkyl and alkenyl group is from 1 to 3.

Particularly preferred examples of $R_1$ to $R_{10}$ include an alkyl group such as methyl and ethyl, an aryl group such as phenyl, an alkenyl group such as propenyl, and an aralkyl group such as benzyl.

These linking groups may be linked to Q either directly or via a straight or branched chain alkylene group, e.g., a methylene group, an ethylene group, a propylene group, a butylene group, a hexylene group, a 1-methylethylene group, etc.

Group A specifically includes a straight or branched chain alkylene group, e.g., a methylene group, an ethylene group, a propylene group, a butylene group, a hexylene group, a 1-methylethylene group, etc.; a straight or branched chain alkenylene group, e.g., a vinylene group, a 1-methylvinylene group, etc.; a straight or branched chain aralkylene group, e.g., a benzylidene group, etc.; or an arylene group, e.g., a phenylene group, a naphthylene group, etc.; and a linking group formed by any combination of these groups and the above-described X group. The group A preferably contains up to 12 carbon atoms, and more preferably up to 7 carbon atoms, and most preferably up to 3 carbon atoms.

Specific examples of the substituted or unsubstituted amino group (inclusive of its salt) represented by B include an amino group or a hydrochloride thereof, a methylamino group, a dimethylamino group or a hydrochloride thereof, a diethylamino group, a dibutylamino group, a dipropylamino group, an N-dimethylaminoethyl-N-methylamino group, etc. The nitrogen-containing heterocyclic ring as represented by B is a 5- or 6-membered heterocyclic ring containing at least one nitrogen atom and optionally a sulfur and/or oxygen atom and may be an aromatic, saturated or unsaturated heterocyclic group. The heterocyclic group may be substituted with an alkyl group or a halogen atom. Specific examples of the nitrogen-containing heterocyclic ring as represented by B include a 1-morpholino group, a 1-piperidino group, a 2-pyridyl group, a 4-pyridyl group, a 1-imidazolyl group, a 2-imidazolyl group, a 1-pyrazolyl group, etc.

M specifically represents a hydrogen atom, an alkali metal atom, e.g., a sodium atom, a potassium atom, etc.; or an ammonium group, e.g., a trimethylammonium group, a dimethylbenzylammonium group, etc.

Of the compounds represented by formula (I), preferred are those represented by formula (II)

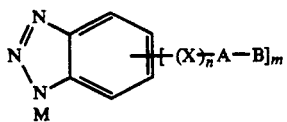
(II)

and those represented by formula (III)

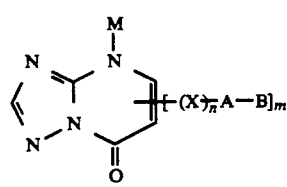
(III)

wherein X, A, B, M, m and n are as defined in formula (I).

In formulae (II) and (III), the heterocyclic rings may be substituted with the substituent groups for the heterocyclic group formed by Q in formula (I).

Specific but non-limiting examples of the compounds represented by formula (I), (II) or (III) are shown below.

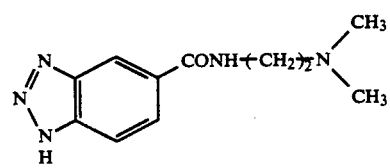
1.

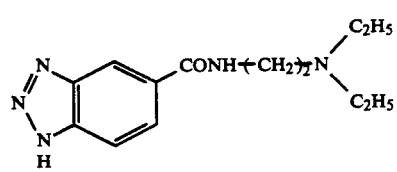
2.

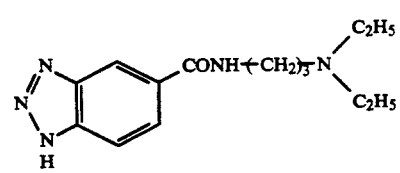
3.

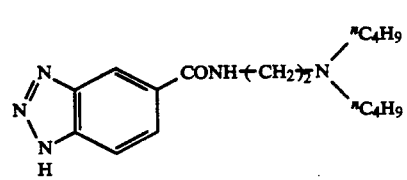
4.

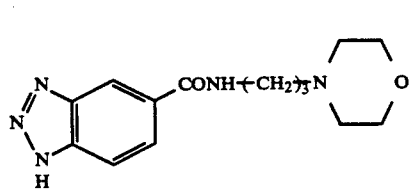
5.

-continued

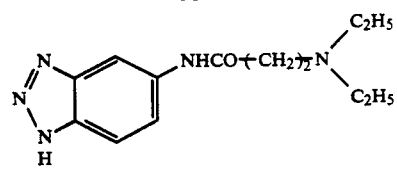
6.

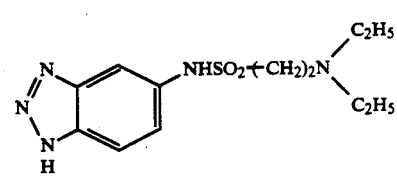
7.

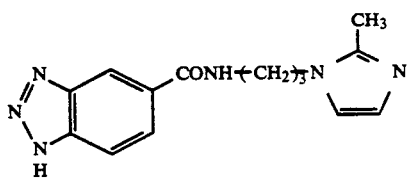
8.

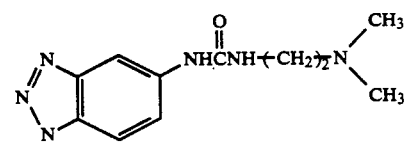
9.

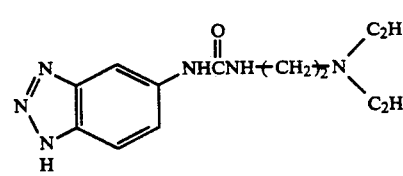
10.

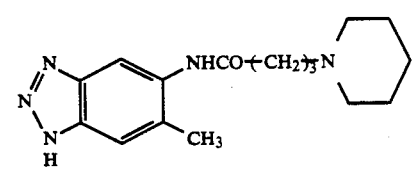
11.

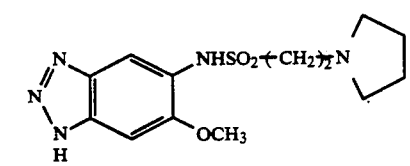
12.

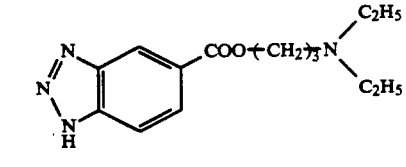
13.

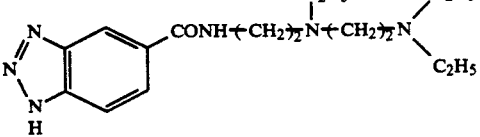
14.

-continued
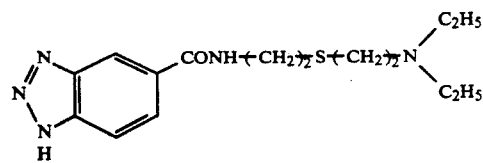 15.
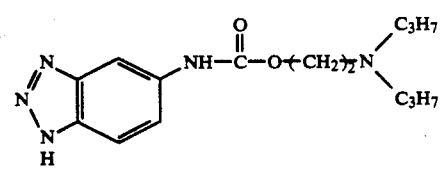 16.
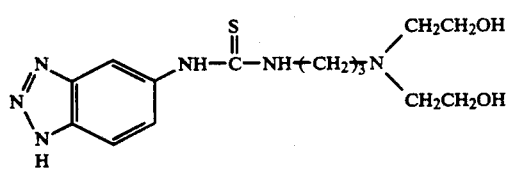 17.
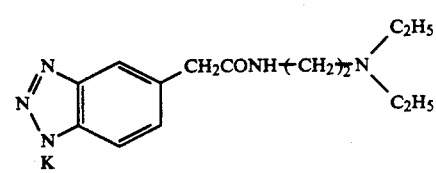 18.
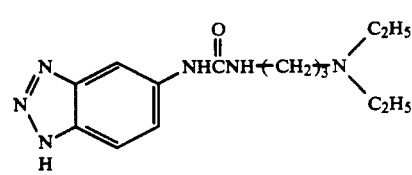 19.
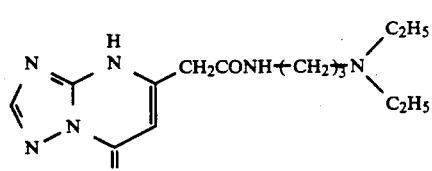 20.
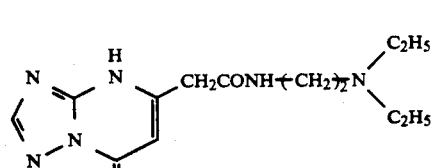 21.
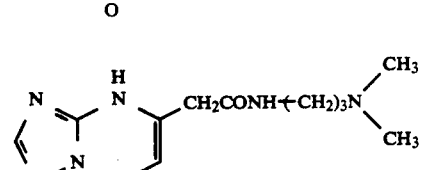 22.
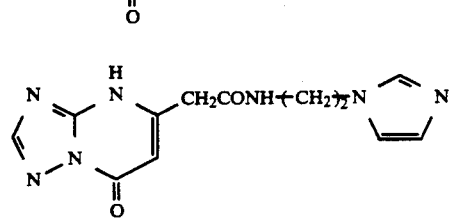 23.
-continued
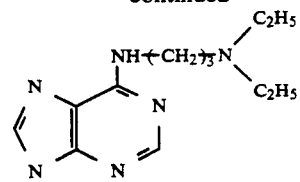 24.
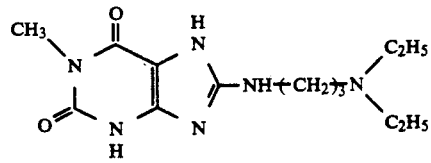 25.
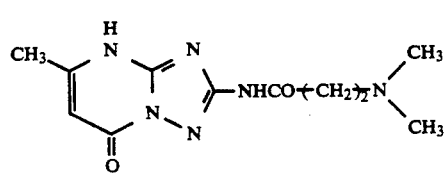 26.
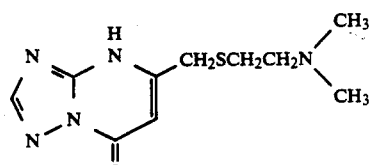 27.
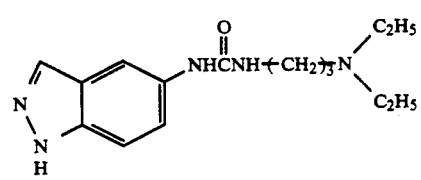 28.
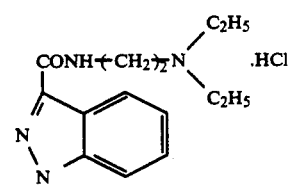 29.
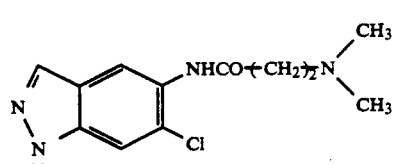 30.
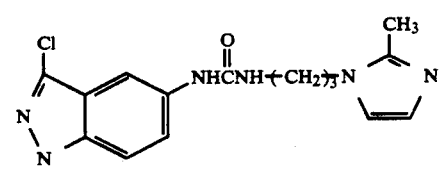 31.
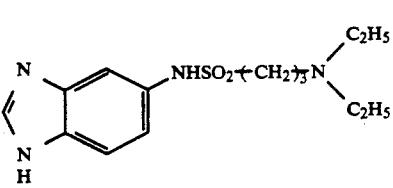 32.

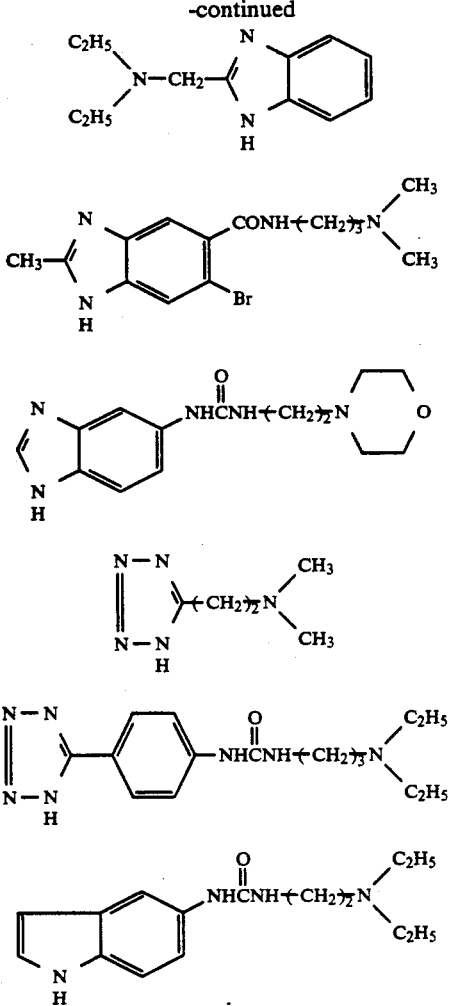

The compounds according to the present invention can be synthesized by the processes described, e.g., in Japanese Patent Publication Nos. 29390/85 and 29391/85, Japanese Patent Application (OPI) Nos. 159162/84, 217358/85, 162235/83, and 83420/79 (the term "OPI" as used herein refers to a "published unexamined Japanese patent application"), and U.S. Pat. Nos. 3,082,088 and 4,311,781. Typical examples of syntheses of the compounds are given below.

SYNTHESIS EXAMPLE 1

Synthesis of Compound (1)

To a mixture of 11.2 g of 5-phenoxycarbonylbenzotriazole and 4.4 g of N,N-dimethylethylenediamine was added 150 ml of benzene, followed by heat-refluxing for 4 hours. After cooling to room temperature, the precipitated crystals were collected by filtration and recrystallized from methanol to obtain 7.9 g of Compound (1) having a melting point of 182° to 184° C.

SYNTHESIS EXAMPLE 2

Synthesis of Compound (2)

To 60.0 g of 5-phenoxycarbonylbenzotriazole were added 500 ml of acetonitrile and 32.0 g of N,N-diethylethylenediamine, and the mixture was heat-refluxed for 4 hours. After the reaction, the reaction mixture was stirred in an ice bath. The precipitated crystals were collected by filtration and recrystallized from 400 ml of methanol to obtain 56.1 g of Compound (2) having a melting point of 164° to 165° C.

SYNTHESIS EXAMPLE 3

Synthesis of Compound (3)

To 23.9 g of 5-phenoxycarbonylbenzotriazole were added 200 ml of acetonitrile and 14.3 g of N,N-diethyltrimethylenediamine, and the mixture was heated at reflux for 4 hours. After the reaction, the reaction mixture was stirred in an ice bath. The precipitated crystals were collected by filtration and recrystallized from 200 ml of a mixed solvent of acetonitrile and ethanol (1:1 by volume) to obtain 23.0 g of Compound (3) having a melting point of 104° to 108° C.

SYNTHESIS EXAMPLE 4

Synthesis of Compound (5)

To 23.9 g of 5-phenoxycarbonylbenzotriazole were added 200 ml of acetonitrile and 15.8 g of 3-aminopropylmorpholine, and the mixture was heated at reflux for 4 hours. After the reaction, the reaction mixture was concentrated to dryness under reduced pressure, and the resulting oily substance was recrystallized from 250 ml of a mixed solvent of ethanol, ethyl acetate, and n-hexane (4:3:3 by volume) to obtain 23.4 g of Compound (5) having a melting point of 136° to 138° C.

SYNTHESIS EXAMPLE 5

Synthesis of Compound (8)

To 23.9 g of 5-phenoxycarbonylbenzotriazole were added 200 ml of acetonitrile and 15.3 g of 1-(3-aminopropyl)-2-methylimidazole, and the mixture was heat-refluxed for 4 hours. After the reaction, the reaction mixture was stirred in an ice bath, and the precipitated crystals were recrystallized from 200 ml of methanol to obtain 15.9 g of Compound (8) having a melting point of 231° to 233° C.

SYNTHESIS EXAMPLE 6

Synthesis of Compound (10)

To 62.1 g of 5-aminobenzotriazole dihydrochloride was added 500 ml of dimethylacetamide, and 83,7 ml of triethylamine was added dropwise thereto while being cooled in an ice bath. To the mixture was further added dropwise 21.0 ml of pyridine, and 42.3 g of phenyl chlorocarbonate was then added dropwise thereto while maintaining the system at 5° C. or lower, followed by stirring at room temperature for 2 hours. After the reaction, the reaction mixture was poured into 2 ( of icewater for crystallization, followed by filtration to obtain 60.8 g of 5-phenoxycarbonylaminobenzotriazole.

To the resulting compound (5.1 g) was added 40 ml of acetonitrile, followed by stirring for 5 minutes at 45° C. To the mixture was added dropwise 2.6 g of N,N-diethylethylenediamine while stirring, and the stirring was continued for an additional 2 hours. The reaction mixture was cooled in an ice bath, and the precipitated crystals were collected by filtration and recrystallized from 60 ml of a mixed solvent of methanol and acetonitrile (1:5 by volume) to obtain 3.8 g of Compound (10) having a melting point of 149° to 150° C.

SYNTHESIS EXAMPLE 7

Synthesis of Compound (19)

To 7.6 g of 5-phenoxycarbonylaminobenzotriazole as prepared in Synthesis Example 6 was added 40 ml of acetonitrile, followed by stirring at 45° C. To the mixture was added dropwise 4.8 g of N,N-diethyltrimethylenediamine while stirring at 45° C., and the stirring was continued for an additional 3 hours at 45° C. After the reaction, the reaction mixture was cooled in an ice bath, and the precipitated crystals were filtered and recrystallized from 55 ml of a mixed solvent of methanol and acetonitrile (3:8 by volume) to obtain 5.4 g of Compound (19) having a melting point of 151° to 152° C.

SYNTHESIS EXAMPLE 8

Synthesis of Compound (9)

To 7.6 g of 5-phenoxycarbonylaminobenzotriazole as prepared in Synthesis Example 6 was added 40 ml of acetonitrile, followed by stirring at 40° C. To the mixture was added dropwise 3.2 g of N,N-dimethylethylenediamine while stirring at 40° C., and the stirring was continued for an additional one hour at 40° C. The reaction mixture was cooled in an ice bath, and the precipitated crystals were collected by filtration and recrystallized from 130 ml of a mixed solvent of methanol and dimethylformamide (10:3 by volume) to obtain 4.1 g of Compound (9) having a melting point of 207° to 210° C.

SYNTHESIS EXAMPLE 9

Synthesis of Compound (27)

To 28.3 g of 2-dimethylaminoethanethiol hydrochloride was added 200 ml of acetonitrile, and 80 ml of a 28 wt % solution of sodium methoxide in methanol was added thereto in a water bath at 20° C. Further, 32.9 g of ethyl 4-chloroacetacetate was added dropwise thereto while cooling in an ice bath. After the addition was completed, the mixture was stirred at 40° C. for 2 hours, followed by filtration to remove the inorganic salts. The filtrate was concentrated to dryness under reduced pressure, and the resulting oily substance was purified by silica gel column chromatography using a chloroform/methanol mixture (10:1 by volume) as a developing solvent to obtain 41.8 g of ethyl 4-(2-dimethylaminoethylthio)acetacetate.

To the resulting product (23.3 g) were added 8.4 g of 3-amino-1,2,4-triazole and 4.0 ml of acetic acid, and the mixture was heat-refluxed for 4 hours. After the reaction, 100 ml of methanol was added to the reaction mixture, followed by stirring for 1 hour in an ice bath. The precipitated crystals were collected by filtration and recrystallized from 300 ml of methanol to obtain 10.2 g of Compound (27) having a melting point of 109° to 110° C.

SYNTHESIS EXAMPLE 10

Synthesis of Compound (20)

To a mixture of 19.4 g of 6-carboxymethyl-4-hydroxy-1,3,3a,7-tetraazaindene and 14.3 g of N,N-diethyltrimethylenediamine was added 250 ml of dimethylformamide, and 22.6 g of dicyclohexylcarbodiimide was added dropwise to the mixture at room temperature. The stirring was continued for 5 hours, and the precipitated crystals were removed by filtration. The filtrate was concentrated to dryness under reduced pressure, and the resulting solid was recrystallized from 400 ml of a 1:1 (by volume) mixture of methanol and acetone to obtain 18.0 g of Compound (20) having a melting point of 214° to 215° C.

According to the development processing of the present invention, an exposed silver halide photographic material is processed with a known developing solution in the presence of the compound represented by formula (I). It is preferred that the compound be incorporated into light-sensitive materials, and particularly emulsion layers or other hydrophilic colloidal layers, in the course of their preparation, or that the compound be incorporated into a developer or a prebath thereof. It is more preferred for the compound to be originally incorporated into the light-sensitive materials. Examples of light-sensitive material include black-and-white negative film, color negative films, X-ray films, graphic arts films and the like.

Incorporation of the compound of the present invention can be carried out by dissolving it in water or an appropriate water-miscible organic solvent, such as alcohols, ethers, glycols, ketones, esters, amides, and the like. The compound should be added in an amount at least sufficient to produce significant inhibition of fog. Such an amount usually ranges from about $10^{-7}$ to $10^{-2}$ mol, and preferably from about $10^{-6}$ to $10^{-2}$ mol, per mol of silver in the case of addition of a light-sensitive material, and from about $10^{-6}$ to $10^{-1}$ mol, and preferably from about $10^{-5}$ to $3 \times 10^{-2}$ mol, per liter of a processing solution in the case of addition to a developer or a prebath thereof.

Surface latent image type silver halide emulsions which can be used in the present invention are generally prepared by mixing a water-soluble silver salt, e.g., silver nitrate, and a water-soluble halogen salt, e.g., potassium bromide, in the presence of a solution of a water-soluble high polymer, e.g., gelatin. The silver halide used is not limited, and includes silver chloride, silver bromide and, in addition, mixed silver halides, e.g., silver chlorobromide, silver iodobromide, silver chloroiodobromide, etc.

The silver halide grains of the emulsion preferably have a mean grain size of about 2 μm or smaller, and more preferably about 0.4 μm or smaller, in terms of diameter for spherical or nearly spherical grains or edge length for cubic grains, being averaged based on a projected area. The grain size distribution may be either narrow or broad.

The silver halide grains may have any crystal form, such as a cubic form, an octahedral form, a composite form thereof, and tabular form as described in Japanese Patent Application (OPI) Nos. 127921/83 and 113926/83. Further, they may have a homogeneous structure throughout the individual grains or a heterogeneous layered structure. Conversion type grains as described in British Patent 635,841 and U.S. Pat. No. 3,622,318 may also be used.

Two or more different silver halide emulsions separately prepared may be used as a mixture thereof.

During the formation of silver halide grains or their physical ripening, a cadmium salt, a zinc salt, a lead salt, a thallium salt, an iridium salt or a complex salt thereof, a rhodium salt or a complex salt thereof, an iron salt or a complex salt thereof, etc. may be present in the system.

The silver halide emulsion may be used in its primitive form, but is usually subjected to chemical sensitization. Chemical sensitization can be carried out by sulfur sensitization using active gelatin or a compound containing sulfur capable of reacting with silver (e.g., thiosulfates, thioureas, mercapto compounds, rhodanines, etc.), reduction sensitization using a reducing substance (e.g., stannous salts, amines, hydrazine derivatives, formamidinesulfinic acid, silane compounds, etc.), noble metal sensitization using a noble metal compound (e.g., gold compounds, complex salts of the group VIII elements, e.g., platinum, iridium, palladium, etc.) or a combination thereof.

Binders or protective colloids which can be used in the emulsion layers or intermediate layers of the light-sensitive materials typically include gelatin, although hydrophilic colloids may also be employed. Examples of useful hydrophilic colloids other than gelatin include proteins, such as gelatin derivatives, graft polymers of gelatin and other high polymers, albumin, casein, etc.; cellulose derivatives, such as hydroxyethyl cellulose, carboxymethyl cellulose, cellulose sulfate, etc.; sugar derivatives, e.g., sodium alginate, dextran, starch derivatives, etc.; and a wide variety of synthetic hydrophilic high polymers, such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc., and copolymers of monomers constituting these homopolymers.

The gelatin used includes not only lime-processed gelatin but also acid-processed gelatin and enzyme-processed gelatin. Hydrolysis products or enzymatic decomposition products of gelatin may also be used.

The emulsion layers or other hydrophilic colloidal layers of the photographic materials processed according to the present invention can contain organic or inorganic hardening agents, such as chromium salts (e.g., chromium alum, chromium acetate, etc.), aldehydes (e.g., formaldehyde, glyoxal, glutaraldehyde, etc;), N-methylol compounds (e.g., dimethylolurea, methyloldimethylhydantoin, etc.), dioxane derivatives (e.g., 2,3-dihydroxydioxane, etc.), active vinyl compounds (e.g., 1,3,5-triacryloyl-hyxahydro-s-triazine, 1,3-vinylsulfonyl-2-propanol, etc.), active halogen compounds (e.g., 2,4-dichloro-6-hydroxy-s-triazine, etc.), mucohalogenic acids (e.g., mucochloric acid, mucophenoxychloric acid, etc.), N-carbamoylpyridinium salts (e.g., (1-morpholinocarbonyl-3-pyridinio)methanesulfonate, etc.), and the like, either individually or in a combination thereof. Preferred hardening agents are active vinyl compounds and active halogen compounds.

The photographic emulsion layers and other hydrophilic colloidal layers can further contain various surface active agents for various purposes, such as coating aids, for static charge prevention, improvement of slipperiness, emulsification and dispersion aids, prevention of adhesion, improvement of photographic characteristics (e.g., development acceleration, increase in contrast, and increase in sensitivity), and the like. Examples of useful surface active agents include nonionic surface active agents, such as saponin (steroid type), alkylene oxide derivatives (e.g., polyethylene glycol, polyethylene glycol/polypropylene glycol condensates, polyethylene glycol alkyl ethers or aryl ethers, polyethylene glycol esters, polyethylene glycol sorbitan esters, polyalkylene glycol alkylamines or amides, polyethylene oxide adducts of silicone, etc.), glycidol derivatives (e.g., alkenylsuccinic polyglycerides, alkylphenyl polyglycerides, etc.), fatty acid esters of polyhydric alcohols, alkyl esters of sugars, and the lile; anionic surface active agents containing an acid radical, such as carboxyl, sulfo, phospho, sulfate, phosphate and like groups, e.g., alkylcarboxylates, alkylsulfonates, alkylbenzenesulfonates, alkylnaphthalenesulfonates, alkylsulfates, alkylphosphates, N-acyl-N-alkyltaurines, sulfosuccinates, sulfoalkylpolyoxyethylene alkyl phenyl ethers, polyoxyethylene alkylphosphates, and the like; amphoteric surface active agents, such as amino acids, aminoalkylsulfonic acids, aminoalkyl sulfates or phosphates, alkylbetaines, amine oxides, and the like; and cationic surface active agents, such as alkylamine salts, aliphatic or aromatic quaternary ammonium salts, heterocyclic quaternary ammonium salts, e.g., pyridinium, imidazolium, etc., aliphatic or heterocyclic phosphonium or sulfonium salts, and the like. As antistatic agents, fluorine-containing compounds are particularly preferred.

The photographic emulsions to be used in the present invention may be spectrally sensitized with methine dyes or other dyes, such as cyanine dyes, merocyanine dyes, complex cyanine dyes, complex merocyanine dyes, holopolar cyanine dyes, hemicyanine dyes, styryl dyes, and hemioxonol dyes. Particularly useful dyes are cyanine dyes, merocyanine dyes, and complex merocyanine dyes. Any of nuclei commonly utilized for cyanine dyes can be employed as a basic heterocyclic nucleus in these dyes. Such nuclei include a pyrroline nucleus, an oxazoline nucleus, a thiszoline nucleus, a pyrrole nucleus, an oxazole nucleus, a thiazole nucleus, a selenazole nucleus, an imidazole nucleus, a tetrazole nucleus, a pyridine nucleus, etc.; any of these nuclei to which an alicyclic hydrocarbon ring is fused; and any of these nuclei to which an aromatic hydrocarbon ring is fused, e.g., an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc. These nuclei may have a substituent at the carbon atom thereof.

Merocyanine dyes or complex merocyanine dyes can contain a 5- to 6-membered heterocyclic nucleus having a ketomethylene structure, e.g., a pyrazolin 5 one nucleus, a thiohydantoin nucleus, a 2-thiooxazolidine-2,4-dione nucleus, a thiazolidine-2,4-dione nucleus, a rhodanine nucleus, a thiobarbituric acid nucleus, etc. These sensitizing dyes may be used either individually or in combinations thereof. In particular, combinations of sensitizing dyes are often used for the purpose of supersensitization.

For the purpose of increasing sensitivity or contrast or accelerating development, the photographic emulsions may contain, for example, polyalkylene oxides or derivatives thereof, such as ethers, esters, amines, etc., thioether compounds, thiomorpholines, quaternary ammonium salt compounds, urethane derivatives, urea derivatives, imidazole derivatives, 3-pyrazolidones, and so on.

For the purpose of improving dimensional stability and the like, the photographic emulsion layers or other hydrophilic colloidal layers may further contain a dispersion of a water-soluble or sparingly water-soluble synthetic polymer. Such a polymer includes homo- or copolymers of alkyl (meth)acrylates, glycidyl (meth)acrylates, styrene, etc., and copolymers of these monomers and acrylic acid, methacrylic acid, etc.

The hydrophilic colloidal layers of the light-sensitive materials used may contain a water-soluble dye as a filter dye or for other purposes, for example, prevention of irradiation. Such water-soluble dyes include oxonol dyes, hemioxonol dyes, styryl dyes, merocyanine dyes, cyanine dyes, and azo dyes, with oxonol dyes, hemioxonol dyes, and merocyanine dyes being particularly useful.

For the purpose of preventing fog during preparation, preservation or photographic processing of the light-sensitive material or for stabilizing photographic performance, the photographic emulsions can contain a variety of compounds known as antifoggants or stabilizers in addition to the compounds of formula (I) according to the present invention. Examples of these compounds are azoles, e.g., benzothiazolium salts, nitroimidazoles, nitrobenzimidazoles, chlorobenzimidazoles, bromobenzimidazoles, nitroindazoles, benzotriazoles, aminotriazoles, etc.; mercapto compounds, e.g., mercaptothiazoles, mercaptobenzothiazoles, mercaptobenzimidazoles, mercaptothiadiazoles, mercaptotetrazoles (especially 1-phenyl-5-mercaptotetrazole), mercaptopyrimidines, mercaptotriazines, etc.; thioketo compounds, e.g., oxazolinethione, etc.; azaindenes, e.g., triazaindenes, tetraazaindenes (especially, 4-hydroxy-substituted(1,3,3a,7)tetraazaindenes), pentaazaindenes, etc.; benzenethiosulfonic acid, benzenesulfinic acid, benzenesulfonic acid amide; and so on. Each of the antifoggant and the stabilizer can be used in an amount approximately equivalent to the amount of the compound of formula (I).

The light-sensitive materials may contain dye image forming couplers, i.e., compounds capable of developing a color upon oxidative coupling with an aromatic primary amine developing agent (e.g., phenylenediamine derivatives and aminophenol derivatives) when subjected to color development processing. The couplers to be used preferably have a hydrophobic group called a "ballast group" by which the molecule is rendered non-diffusible, or they preferably have a polymerized form. The couplers may be either 4-equivalent or 2-equivalent with reference to silver ions. The light-sensitive materials may further contain colored couplers having color correction effects, so-called DIR couplers that are capable of releasing a development inhibitor upon development processing, or colorless DIR coupling compounds which produce a colorless product by a coupling reaction to release a developing inhibitor.

Magenta forming couplers to be used include 5-pyrazolone couplers, pyrazolotriazole couplers, pyrazolobenzimidazole couplers, cyanoacetylcumarone couplers, open-chain acylacetonitrile couplers, etc. Yellow forming couplers to be used include acrylacetamide couplers (e.g., benzoylacetanilides and pivaloylacetanilides). Cyan forming couplers to be used include naphthol couplers and phenol couplers.

In order to satisfy particular requirements, two or more of these couplers may be incorporated into the same layer, or two or more layers may contain the same coupler.

The introduction of couplers into silver halide emulsion layers can be carried out by known methods, such as the method described in U.S. Pat. No. 2,322,027. For example, the coupler can be dissovled in a high-boiling organic solvent, such as alkyl phthalates.(e.g., dibutyl phthalate, dioctyl phthalate, etc.), phosphoric esters (e.g., diphenyl phosphate, triphenyl phosphate, tricresyl phosphate, dioctylbutyl phosphate, etc.), citric esters (e.g., acetyl tributyl citrate), benzoic esters (e.g., octyl benzoate), alkylamides (e.g., diethyl laurylamide), fatty acid esters (e.g., dibutoxyethyl succinate, diethyl azelate, etc.), and trimesic esters (e.g., tributyl trimesate); or a low-boiling organic solvent having a boiling point of from about 30° C. to 150° C., such as lower alkyl acetates (e.g., ethyl acetate, butyl acetate, etc.), ethyl propionate, sec-butyl alcohol, methyl isobutyl ketone, β-ethoxyethyl acetate, and methyl cellosolve acetate; or a mixture thereof, and the solution is dispersed in a hydrophilic colloid.

Introduction of couplers can also be effected in accordance with the dispersion method using polymers described in Japanese Patent Publication No. 39853/76 and Japanese Patent Application (OPI) No. 59943/76.

When the coupler has an acid radical, e.g., a carboxyl group or a sulfo group, it is introduced into a hydrophilic colloid in the form of an alkaline aqueous solution.

The light-sensitive materials can contain known discoloration inhibitors, such as hydroquinone derivatives, gallic acid derivatives, p-alkoxyphenols, p-oxyphenol derivatives, and bisphenols.

In addition to the aforesaid additives, the light-sensitive materials can contain various other additives according to the purpose. Specific examples of the additives which can be used in the present invention are described in Research Disclosure, No. 17643 (December, 1978) and ibid, No. 18716 (November, 1979) as tabulated below:

| Kind | Photographic Additives | |
| --- | --- | --- |
|  | RD 17643 | RD 18716 |
| Chemical sensitizer | p. 23 | p. 648 right column (RC) |
| Sensitivity increasing agent |  | p. 648 right column (RC) |
| Spectral sensitizer and supersensitizer | pp. 23–24 | p. 648 RC–p. 649 RC |
| Brightening agent | p. 24 |  |
| Antifoggant and stabilizer | pp. 24–25 | p. 649 RC |
| Light absorbent, filter dye, and ultraviolet absorbent | pp. 25–26 | p. 649 RC–p. 650 left column (LC) |
| Stain inhibitor | p. 25 RC | p. 650 LC–RC |
| Dye image stabilizer | p. 25 |  |
| Hardening agent | p. 16 | p. 651 RC |
| Binder | p. 26 | " |
| Plasticizer and lubricant | p. 27 | p. 650 RC |
| Coating aid and surface active agent | pp. 26–27 | " |
| Antistatic agent | p. 27 | " |

Photographic processing of the silver halide photographic material, whether for black-and-white image formation or for color image formation, can be carried out in a known manner with known processing solutions, provided that development is effected in the presence of the compound according to the present invention. The processing temperature is usually between about 18° C. and 50° C., but temperatures lower than 18° C. or higher than 50° C. may also be employed.

A black-and-white developer contains one or more known developing agents, such as dihydroxybenzenes (e.g., hydroquinone), 3-pyrazolidones (e.g., 1-phenyl-3-pyrazolidone), and aminophenols (e.g., N-methyl-p-aminophenol).

A color developer generally is an alkaline aqueous solution containing, as a main component, a known aromatic primary amine developing agent. Useful color developing agents include, for example, phenylenediamine compounds, e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline, 4-amino-3-methyl-N-ethyl-N-β-methoxyethylaniline, etc. Other developing agents, such as those described in L. F. A. Mason, *Photographic Processing Chemistry*, 226-229 (Focal Press, 1966), U.S. Pat. Nos. 2,193,015 and 2,592,364, and Japanese Patent Application (OPI) No. 64933/73, may also be employed.

The developers generally contain pH buffers, such as sulfites, carbonates, borates or phosphates of alkali metals, and developing inhibitors or antifoggants, such as bromides, iodides, and organic antifoggants other than the compounds of the present invention. If desired, the developers may further contain water softeners; preservatives, e.g., hydroxylamines, etc.; organic solvents, e.g., benzyl alcohol, diethylene glycol, etc.; development accelerators, e.g., polyethylene glycol, quaternary ammonium salts, amines, etc.; color forming couplers; competing couplers; nucleating agents, e.g., sodium boron hydride, etc.; auxiliary developing agents, e.g., 1-phenyl-3-pyrazolidone, etc.; tackifiers; polycarboxylic acid type chelating agents disclosed in U.S. Pat. No. 4,083,723; and antioxidants, e.g., those described in Wester German Patent Publication No. 2,622,950.

In color photographic processing, the photographic emulsion layers after color development are usually subjected to bleaching. Bleaching may be effected simultaneously with fixation, or these two steps may be carried out separately. Useful bleaching agents include compounds of polyvalent metals, e.g., iron (III), cobalt (III), chromium (VI), copper (II), etc., peracids, quinones, nitroso compounds, and the like. Examples of these bleaching agents are ferricyanides; bichromates; organic complex salts of iron (III) or cobalt (III), such as complex salts with aminopolycarboxylic acids, e.g., ethylenediaminetetraacetic acid, nitrilotriacetic acid, 1,3-diamino-2-propanoltetracetic acid, etc., or organic acids, e.g., citric acid, tartaric acid, malic acid, etc.; persulfates; manganates; nitrosophenol; and so on. Of these, sodium (ethylenediaminetetraacetato)iron (III), and ammonium (ethylenediaminetetraacetato)iron (III) are particularly useful. In particular, (ethylenediaminetetraacetato)iron (III) salts are useful in both a separate bleaching bath and a bleach-fix monobath.

The bleaching or bleach-fix bath can contain a bleaching accelerator as described in U.S. Pat. Nos. 3,042,520 and 3,241,966 and Japanese Patent Publication Nos. 8506/70 and 8836/70, a thiol compound as described in Japanese Patent Application (OPI) No. 65732/78, and various other additives.

The present invention will now be illustrated in greater detail by way of the following examples, but the present invention is not to be construed as being limited thereto. Unless otherwise indicated, all parts, percents and ratios are by weight.

EXAMPLE 1

A silver iodobromide-gelatin emulsion containing 1.5 mol % of silver iodide (mean grain size: 0.9 μm) was chemically sensitized by adding sodium thiosulfate and potassium chloroaurate. To the resulting emulsion was added 3,3'-disulfopropyl-5,5'-dichloro-9-ethyl-oxacarbocyanine sodium salt, and then a compound of the present invention or a comparative compound was added thereto as shown in Table 1. A coating aid (sodium dodecylbenzenesulfonate) and a hardening agent (2,4-dichloro-6-hydroxy-s-triazine) were further added to the emulsion. The resulting coating composition was coated on a cellulose triacetate support and dried to obtain Samples 1 to 12.

Each of Samples 1 to 12 was exposed to light through an optical wedge having a yellow filter for 1/20 second by means of a sensitometer. The exposed sample was developed with a PQ developer having the formulation shown below at 35° C. for 35 seconds, followed by fixation, washing, and drying in a usual manner. The photographic properties were evaluated by determining sensitivity and fog, and the results obtained are shown in Table 1. In the Table, photographic sensitivity is a reciprocal of a logarithmic of an exposure required for obtaining an optical density of fog +0.2, and the results are relatively expressed taking the sensitivity of Sample 1 as 100 (standard).

| Formulation of Developer: | |
|---|---|
| Sodium sulfite | 40 g |
| Hydroquinone | 25 g |
| Boric acid | 10 g |
| 1-Phenyl-3-pyrazolidone | 1.5 g |
| Potassium hydroxide | 30 g |
| 5-Methylbenzotriazole | 0.15 g |
| Glutaraldehyde bisulfite | 15 g |
| Acetic acid | 12 g |
| Potassium bromide | 10 g |
| Water to make | 1 l |

TABLE 1

| Sample No. | Compound Added | Amount added (mol/mol-AgX) | Fog | Relative Sensitivity |
|---|---|---|---|---|
| 1 | — | — | 0.25 | 100 |
| 2 | Compound 1 | $4.5 \times 10^{-4}$ | 0.18 | 96 |
| 3 | " | $18.0 \times 10^{-4}$ | 0.10 | 92 |
| 4 | " | $54.0 \times 10^{-4}$ | 0.06 | 86 |
| 5 | Compound 10 | $18.0 \times 10^{-4}$ | 0.11 | 91 |
| 6 | " | $54.0 \times 10^{-4}$ | 0.06 | 84 |
| 7 | Compound 5 | $54.0 \times 10^{-4}$ | 0.06 | 89 |
| 8 | Compound 20 | $54.0 \times 10^{-4}$ | 0.14 | 88 |
| 9 | Compound 27 | $54.0 \times 10^{-4}$ | 0.10 | 87 |
| 10 | Compound 36 | $54.0 \times 10^{-4}$ | 0.10 | 87 |
| 11 | Comparative Compound (a)* | $18.0 \times 10^{-4}$ | 0.06 | 72 |
| 12 | Comparative Compound (b)** | $54.0 \times 10^{-4}$ | 0.20 | 88 |

Note:
*Comparative Compound (a)

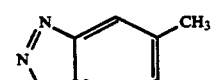

**Comparative Compound (b)

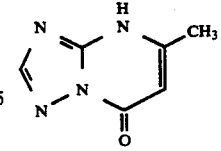

As is apparent from Table 1, Samples 4, 6, and 7 according to the present invention show a fog preventing effect equal to that of Sample 11 using Comparative Compound (a) but undergo reduction in sensitivity to lesser degrees as compared with Sample 11. Further, Samples 7, 8, 9, 10, and 11 according to the present invention undergo reduction in sensitivity to the same degree as observed in Sample 12 using Comparative Compound (b) but inhibit fog more significantly than Sample 12.

It can be seen from these observations that the compounds of the present invention are less causative of sensitivity reduction than Comparative Compounds (a) and (b) which are broadly employed antifoggants, while exhibiting fog inhibitory effects to the same degree as produced by these known antifoggants.

Further, the reflection spectra of the unexposed samples revealed that Samples 11 and 12 show greater reduction of absorption of the sensitizing dye as compared with Sample 1, while Samples 2 to 10 show lesser reduction of absorption, indicating that the compounds of the present invention are less causative of hindrance to adsorption of a sensitizing dye.

EXAMPLE 2

To a silver iodobromide-gelatin emulsion containing 7.5 mol % of silver iodide (mean grain size: 0.6 μm) were added potassium chloroaurate, ammonium thiocyanate, and sodium thiosulfate, and the emulsion was heated at 60° C. for 60 minutes to effect chemical sensitization.

A compound of the present invention or a comparative compound was added to the resulting emulsion as shown in Table 2, and the following additives were further added thereto.

Additives:
Coupler: 1-(2,4,6-Trichlorophenyl)-3-[3-(2,4-di-t-amylphenoxy)-acetamido]benzamido-5-pyrazolone
Spectral Sensitizer: Bis-[2-[1-ethyl-3-(3-sulfopropyl)-5,6-dichlorobenzimidazole]]trimethinecyanine sodium salt
Hardening Agent: 2,4-Dichloro-6-hydroxy-1,3,5-triazine sodium salt
Coating Aid: Sodium p-dodecylbenzenesulfonate and sodium p-nonylphenoxypoly(ethyleneoxy)propanesulfonate The resulting coating composition was coated on a support and dried to obtain Samples 13 to 16. Each of the samples was exposed to light for 1/20 second through a yellow filter and then subjected to color development processing according to the following procedures. The photographic properties of the processed samples were determined in the same manner as in Example 1, and the results obtained are shown in Table 2.

| Processing Procedure: Processing Step | Time | Temperature |
|---|---|---|
| Color Development | 2'45" | 38° C. |
| Bleaching | 6'30" | |
| Washing | 3'15" | |
| Fixation | 6'30" | |
| Washing | 3'15" | |
| Stabilization | 3'15" | |

The processing solution used in each step had the following formulation.

| Color Developer Formulation: | |
|---|---|
| Sodium nitrilotriacetate | 1.0 g |
| Sodium sulfite | 4.0 g |
| Sodium carbonate | 30.0 g |
| Potassium bromide | 1.4 g |
| Hydroxylamine sulfate | 2.4 g |
| 4-(N-Ethyl-N-β-hydroxyethylamino)-2-methyl-aniline sulfate | 4.5 g |
| Water to make | 1 l |
| Bleaching Bath Formulation: | |
| Ammonium bromide | 160.0 g |
| Aqueous ammonia (28 wt %) | 25.0 ml |
| Sodium (ethylenediaminetetra-acetato)iron | 130.0 g |
| Glacial acetic acid | 14.0 ml |
| Water to make | 1 l |
| Fixing Bath Formulation: | |
| Sodium tetrapolyphosphate | 2.0 g |
| Sodium sulfite | 4.0 g |
| Ammonium thiosulfate (70 wt %) | 175.0 ml |
| Sodium bisulfite | 4.6 g |
| Water to make | 1 l |
| Stabilizing Bath Formulation: | |
| Formalin | 8.0 ml |
| Water to make | 1 l |

TABLE 2

| Sample No. | Compound Added | Amount added (mol/mol-AgX) | Photographic Properties Fog | Relative Sensitivity |
|---|---|---|---|---|
| 13 | — | — | 0.21 | 100 |
| 14 | Compound 1 | $1.8 \times 10^{-3}$ | 0.06 | 85 |
| 15 | Compound 20 | $1.8 \times 10^{-3}$ | 0.06 | 81 |
| 16 | Comparative Compound (a) | $1.8 \times 10^{-3}$ | 0.05 | 76 |

It can be seen from Table 2 that the compounds according to the present invention are advantageous also when applied to color development in that reduction in sensitivity can be suppressed while producing a fog preventing effect equal to that of Comparative Compound (a).

EXAMPLE 3

In order to demonstrate effectiveness of the compounds according to the present invention when added to a developer, Sample 1 as prepared in Example 1 was exposed to light in the same manner as in Example 1 and subjected to development processing in the same manner as in Example 1, except the developer further contained a compound shown in Table 3. The photographic properties of the processed samples are also shown in Table 3.

TABLE 3

| Run No. | Compound Added | Amount added (mol/l of developer) | Photographic Properties Fog | Relative Sensitivity |
|---|---|---|---|---|
| 1 | — | — | 0.26 | 100 |
| 2 | Compound 1 | $8 \times 10^{-4}$ | 0.08 | 92 |
| 3 | Comparative Compound (a) | $1.5 \times 10^{-3}$ | 0.08 | 83 |

As can be seen from Table 3, the compound of the present invention is advantageous in that reduction in sensitivity is suppressed as compared with Comparative Compound (a) with its fog preventing effect being equal to that of Comparative Compound (a).

While the invention has been described in detail and with reference to specific embodiments thereof, it will be apparent to one skilled in the art that various changes and modifications can be made therein without departing from the spirit and scope thereof.

What is claimed is:

1. A method for development processing of a silver halide photographic material, comprising the step of developing a light-sensitive silver halide photographic material comprising a support having thereon at least one surface latent image type silver halide emulsion layer in the presence of a non-cleaving compound represented by formula (I):

wherein Q represents an atomic group necessary for forming a 5- or 6-membered heterocyclic ring which may be fused with an aromatic carboxylic ring, or an aromatic heterocyclic ring, provided that Q is selected from the group consisting of an indazole ring, a benzotriazole ring, an imidazole ring, a tetrazole ring, a tetraazaindene ring, a triazaindene ring, a pentaazaindene ring, a diazaindene ring, a pyrazole ring, and an indole ring; X represents a divalent linking group selected from the group consisting of:

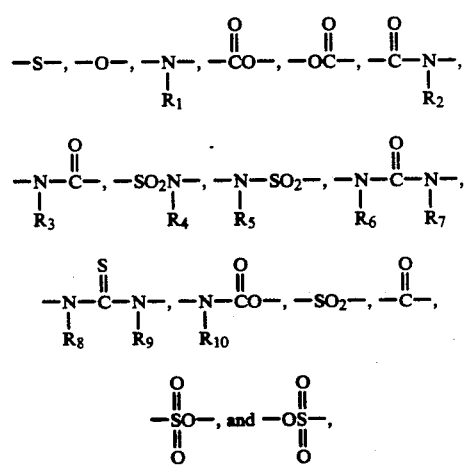

wherein $R_1$, $R_2$, $R_3$, $R_4$, $R_5$, $R_6$, $R_7$, $R_8$, $R_9$, and $R_{10}$, which may be the same or different, each represents a hydrogen atom, a substituted or unsubstituted alkyl group, a substituted or unsubstituted aryl group, a substituted or unsubstituted alkenyl group, or a substituted or unsubstituted aralkyl group, and X is linked to Q via a straight or branched chain alkylene group; A represents a linking group containing at least one group selected from a straight or branched chain alkylene group having at least two carbon atoms, a straight or branched chain alkenylene group, a straight or branched chain aralkylene group and an arylene group; B represents a substituted or unsubstituted amino group or a nitrogen-containing heterocyclic ring selected from the group consisting of a morpholino group, a piperidino group, a pyrrolidino group, a pyridyl group, and an imidazolyl group; M represents a hydrogen atom, an alkali metal atom or an ammonium group; m is 1 or 2; and n is 1.

2. The method as claimed in claim 1, wherein said heterocyclic ring formed by Q is substituted with at least one substituent selected from the group consisting of a nitro group, a halogen atom, a cyano group, a substituted or unsubstituted alkyl group, a substituted or unsubstituted aryl group, a substituted or unsubstituted alkenyl group, a substituted or unsubstituted aralkyl group, a substituted or unsubstituted alkoxy group, a substituted or unsubstituted aryloxy group, a substituted or unsubstituted alkylthio group, a substituted or unsubstituted arylthio group, a substituted or unsubstituted sulfonyl group, a substituted or unsubstituted carbamoyl group, a substituted or unsubstituted sulfamoyl group, a substituted or unsubstituted carbonamido group, a substituted or unsubstituted sulfonamido group, a substituted or unsubstituted acyloxy group, a substituted or unsubstituted sulfonyloxy group, a substituted or unsubstituted ureido group, a substituted or unsubstituted thioureido group, a substituted or unsubstituted acyl group, a substituted or unsubstituted heterocyclic group, a substituted or unsubstituted hydroxycarbonyl group, a substituted or unsubstituted hydroxycarbonylamino group, a substituted or unsubstituted amino group, a carboxyl group, a carboxyl salt, a sulfo group, a sulfo salt, and hydroxyl group.

3. The method as claimed in claim 1, wherein said compound represented by formula (I) is represented by formula (II):

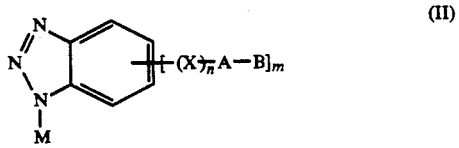

wherein X, A, B, M, m, and n are defined as in formula (I) and the heterocyclic rings of formula (II) may be substituted by at least one substituent selected from the group consisting of a nitro group, a halogen atom, a cyano group, a substituted or unsubstituted alkyl group, a substituted or unsubstituted aryl group, a substituted or unsubstituted alkenyl group, a substituted or unsubstituted aralkyl group, a substituted or unsubstituted alkoxy group, a substituted or unsubstituted aryloxy group, a substituted or unsubstituted alkylthio group, a substituted or unsubstituted arylthio group, a substituted or unsubstituted sulfonyl group, a substituted or unsubstituted carbamoyl group, a substituted or unsubstituted sulfamoyl group, a substituted or unsubstituted carbonamido group, a substituted or unsubstituted sulfonamido group, a substituted or unsubstituted acyloxy group, a substituted or unsubstituted sulfonyloxy group, a substituted or unsubstituted ureido group, a substituted or unsubstituted thioureido group, a substituted or unsubstituted acyl group, a substituted or unsubstituted heterocyclic group, a substituted or unsubstituted hydroxycarbonyl group, a substituted or unsubstituted hydroxycarbonylamino group, a substituted or unsubstituted amino group, a carboxyl group, a carboxyl salt, a sulfo group a sulfo salt, and hydroxyl group.

4. The method as claimed in claim 1, wherein said compound represented by formula (I) is represented by formula (III)

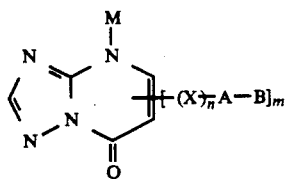

wherein X, A, B, M, m, and n are defined as in formula (I) and the heterocyclic rings of formula (III) may be substituted by at least one substituent selected from the group consisting of a nitro group, a halogen atom, a cyano group, a substituted or unsubstituted alkyl group, a substituted or unsubstituted aryl group, a substituted or unsubstituted alkenyl group, a substituted or unsubstituted aralkyl group, a substituted or unsubstituted alkoxy group, a substituted or unsubstituted aryloxy group, a substituted or unsubstituted alkylthio group, a substituted or unsubstituted arylthio group, a substituted or unsubstituted sulfonyl group, a substituted or unsubstituted carbamoyl group, a substituted or unsubstituted sulfamoyl group, a substituted or unsubstituted carbonamido group, a substituted or unsubstituted sulfonamido group, a substituted or unsubstituted acyloxy group, a substituted or unsubstituted sulfonyloxy group, a substituted or unsubstituted ureido group, a substituted or unsubstituted thioureido group, a substituted or unsubstituted acyl group, a substituted or unsubstituted heterocyclic group, a substituted or unsubstituted hydroxycarbonyl group, a substituted or unsubstituted hydroxycarbonylamino group, a substituted or unsubstituted amino group, a carboxyl group, a carboxyl salt, a sulfo group a sulfo salt, and hydroxyl group.

5. The method as claimed in claim 1, wherein said compound is present in at least one layer of said silver halide photographic material.

6. The method as claimed in claim 5, wherein said compound is present in an amount of from about $10^{-7}$ to $10^{-2}$ mol per mol of silver.

7. The method as claimed in claim 6, wherein said compound is present in an amount of from about $10^{-6}$ to $10^{-2}$ mol per mol of silver in said silver halide.

8. The method as claimed in claim 1, wherein said compound is present in a processing solution selected from a developer solution and a predevelopment bath solution.

9. The method as claimed in claim 8, wherein said compound is present in an amount of from about $10^{-6}$ to $10^{-1}$ mol per liter of said processing solution.

10. The method as claimed in claim 9, wherein said compound is present in an amount of from about $10^{-5}$ to $3 \times 10^{-2}$ mol per liter of said processing solution.

11. The method as claimed in claim 1, wherein said linking group represented by A is selected from a straight or branched chain alkylene group, a straight or branched chain alkenylene group, a straight or branched chain aralkylene group and an arylene group.

12. The method as claimed in claim 11, wherein said linking group represented by A is formed by at least one of the straight or branched chain alkylene group, the straight or branched chain alkenylene group, the straight or branched chain aralkylene group or the arylene group, and at least one of the group selected from the group consisting of

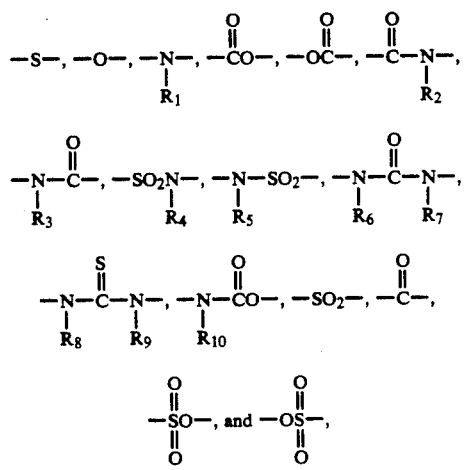

wherein $R_1$, $R_2$, $R_3$, $R_4$, $R_5$, $R_6$, $R_7$, $R_9$, and $R_{10}$, which may be the same or different, each represents a hydrogen atom, a substituted or unsubstituted alkyl group, a substituted or unsubstituted aryl group, a substituted or unsubstituted alkenyl group, or a substituted or unsubstituted aralkyl group.

13. The method as claimed in claim 1, wherein said nitrogen-containing heterocyclic ring represented by B is bonded to the linking group represented by A at the nitrogen atom of said nitrogen-containing heterocyclic ring.

* * * * *